US007544786B2

(12) United States Patent
Aasly et al.

(10) Patent No.: US 7,544,786 B2

(45) Date of Patent: Jun. 9, 2009

(54) POLYNUCLEOTIDE

(75) Inventors: Jan O. Aasly, Trondheim (NO); Zbigniew K. Wszolek, Jacksonville, FL (US); Matthew J. Farrer, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 11 days.

(21) Appl. No.: 10/568,414

(22) PCT Filed: Dec. 19, 2005

(86) PCT No.: PCT/NO2005/000465

§ 371 (c)(1), (2), (4) Date: Jul. 12, 2006

(87) PCT Pub. No.: WO2006/068492

PCT Pub. Date: Jun. 29, 2006

(65) Prior Publication Data

US 2008/0009454 A1 Jan. 10, 2008

(30) Foreign Application Priority Data

Dec. 23, 2004 (NO) ................................ 20045612
May 27, 2005 (NO) ................................ 20052535

(51) Int. Cl.
*C07H 21/02* (2006.01)
*C07H 21/04* (2006.01)

(52) U.S. Cl. ................................ 536/23.1; 536/24.33

(58) Field of Classification Search ....................... None
See application file for complete search history.

(56) References Cited

U.S. PATENT DOCUMENTS 6,420,547 B1 * 7/2002 Maiti et al. ................ 536/24.1

FOREIGN PATENT DOCUMENTS

WO WO 02/081627 * 10/2002
WO WO 2006/068492 6/2006

OTHER PUBLICATIONS

Zimprich et al., [online], 2004, [retrieved on Nov. 26, 2007]. Retrieved from the Internet:< URL: http://www.ncbi.nlm.nih.gov/entrez/viewer.fcgi?db=nuccore&id=55740397>, pp. 1-5.*

GenBank Accession No. AY792511 dated Nov. 15, 2004, 5 pages.

Bonifati et al., "Mutations in the *DJ-I* Gene Associated with Autosomal Recessive Early-Onset Parkinsonism," *Science*, 2003, 299:256-259.

Bosgraaf and Van Haastert, "Roc, a Ras/GTPase domain in complex proteins," *Biochim. Biophys. Acta*, 2003, 1643:5-10.

Chartier-Harlin et al., "α-synuclein locus duplication as a cause of familial Parkinson's disease," *Lancet*, 2004, 364:1167-1169.

Davies et al., "Mutations of the *BRAF* gene in human cancer," *Nature*, 2002, 417:949-954.

de Rijk et al., "Prevalence of Parkinson's disease in the elderly: the Rotterdam Study," *Neurology*, 1995, 45:2143-2146.

Dibb et al., "Switching on kinases: oncogenic activation of BRAF and the PDGFR family." *Nat. Rev. Cancer*, 2004, 4:718-727.

Farrer et al., "Comparison of Kindreds with Parkinsonism and α-Synuclein Genomic Multiplications," *Ann. Neurol.*, 2004, 55:174-179.

Forno, "Neuropathology of Parkinson's Disease," *J. Neuropathol. Exp. Neurol.*, 1996, 55(3):259-272.

Funayama et al., "A New Locus for Parkinson'Disease (*PARK8* ) Maps to Chromosome 12p11.2-q13.1," *Ann. Neurol.*, 2002, 51:296-301.

Gelb et al., "Diagnostic Criteria for Parkinson Disease," *Arch. Neurol.*, 1999, 56:33-39.

Hughes et al., "Accuracy of clinical diagnosis of idiopathic Parkinson's disease: a clinico-pathological study of 100 cases," *J. Neurol. Neurosurg. Psychiatry*, 1992, 55:181-184.

Huse and Kuriyan, "The Conformational Plasticity of Protein Kinases," *Cell*, 2002, 109:275-282.

Kitada et al., "Mutations in the *parkin* gene cause autosomal recessive juvenile parkinsonism," *Nature*, 1998, 392:605-608.

Kong and Cox, "Allele-Sharing Models: LOD Scores and Accurate Linkage Tests," *Am. J. Hum. Genet.*, 1997, 61:1179-1188.

Krüger et al., "Ala30Pro mutation in the gene encoding α-synuclein in Parkinson's disease," *Nat. Genet.*, 1998, 18:106-108.

Lander and Kruglyak, "Genetic dissection of complex traits: guidelines for interpreting and reporting linkage results," *Nat. Genet.*, 1995, 11:241-247.

Lang and Lazano, "Parkinson's Disease. First of Two Parts," *New Engl. J. Med.*, 1998, 339:1044-1053.

Mata et al., "Parkin genetics: one model for Parkinson's disease," *Hum. Mol. Genet.*, 2004, 13:R127-R133.

Paisáan-Ruiz et al., "Cloning of the Gene Containing Mutations that Cause *PARK8*-Linked Parkinson's Disease," *Neuron*, 2004, 44:595-600.

Pals et al., "α-Synuclein Promoter Confers Susceptibility to Parkinson's Disease," *Ann. Neurol.*, 2004, 56:591-595.

Polymeropoulos et al., "Mutation in the α-Synuclein Gene Identified in Families with Parkinson's Disease," *Science*, 1997, 276:2045-2047.

Simon et al., "'Nature versus murture' and incompletely penetrant mutations," *J. Neurol. Neurosurg. Psychiatry*, 2002, 72:686-688.

Singleton et al., "α-Synuclein Locus Triplication Causes Parkinson's Disease," *Science*, 2003, 302:841.

Slatkin and Rannala, "Estimating allele age," *Annu. Rev. Genomics Hum. Genet.*, 2000, 1:225-249.

(Continued)

*Primary Examiner*—Joanne Hama
(74) *Attorney, Agent, or Firm*—Fish & Richardson P.C.

(57) ABSTRACT

A polynucleotide consisting of the base sequence of SEQ ID NO: 2, or a complementary strand thereto, wherein the X is one of the group being defined by the bases A, C or T. A primer and a probe specific for that polynucleotide, wherein the primer and/or probe contains at the least 10 consecutive nucleotides, and finally use of the probe for proving parkinsonism inheritance.

5 Claims, 6 Drawing Sheets

OTHER PUBLICATIONS

Spillantini et al., "α-Synuclein in Lewy bodies," *Nature*, 1997, 388:839-840.

Tanner et al., "Parkinson Disease in Twins: An Etiologic Study," *JAMA*, 1999, 281(4):341-346.

Valente et al., "Hereditary Early-Onset Parkinson's Disease Caused by Mutations in *PINK1*, " *Science*, 2004, 304:1158-1160.

Vila and Przedborski, "Genetic clues to the pathogenesis of Parkinson's disease," *Nat. Med*., 2004, 10 Suppl:S58-S62.

Wirdefeldt et al. "No evidence for heritability of Parkinson disease in Swedish twins," *Neurology*, 2004, 63:305-311.

Zarranz et al., "The New Mutation, E46K, of α-Synuclein Causes Parkinson and Lewy Body Dementia," *Ann. Neurol*, 2004, 55:164-173.

Zimprich et al., "Mutations in *LRRK2* Cause Autosomal-Dominant Parkinsonism with Pleomorphic Pathology," *Neuron*, 2004, 44:601-607.

Zimprich et al., "The PARK8 locus in autosomal dominant parkinsonism: confirmation of linkage and further delineation of the disease-containing interval," *Am. J. Hum. Genet*., 2004, 74:11-19.

* cited by examiner

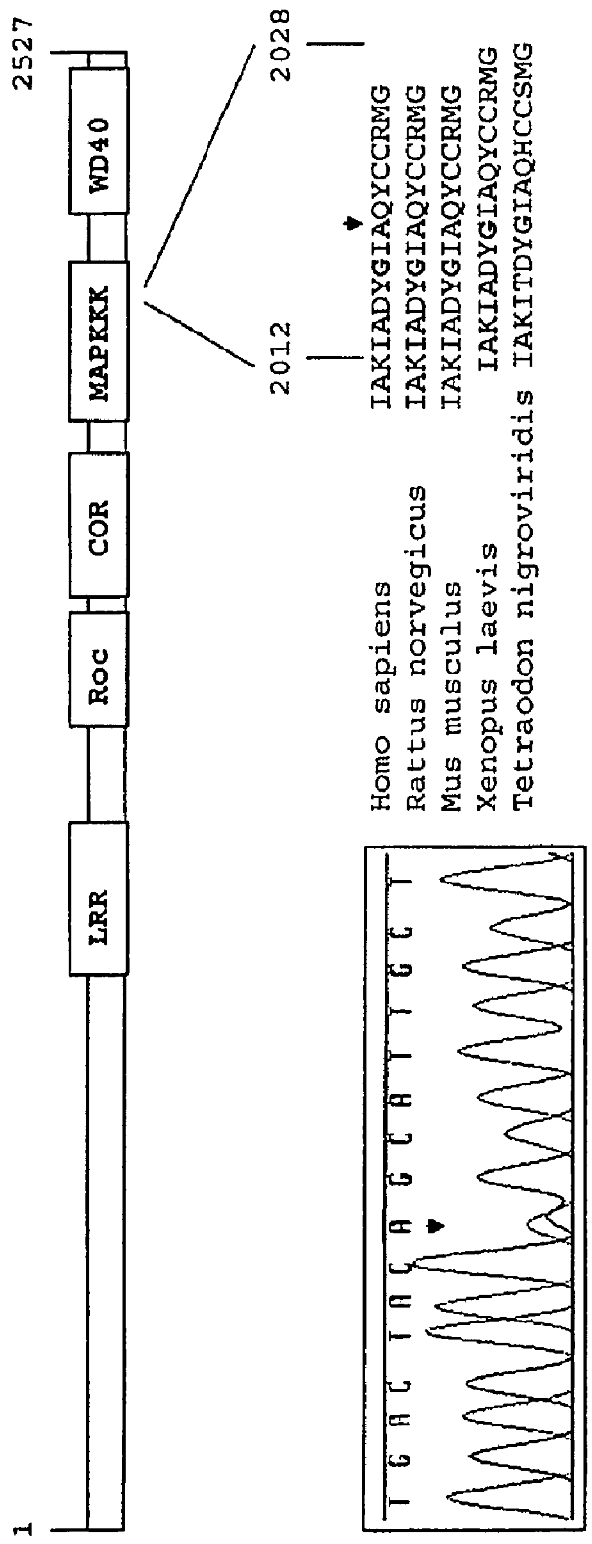

**Figure 1. Schematic drawing of *LRRK2* with predicted protein domains**

(LRR – leucine rich repeat, Roc – Ras in complex proteins, COR – domain C-terminal of Roc, MAPKKK – mitogen-activated protein kinase kinase kinase, WD40 – WD40 repeats). The human *LRRK2* protein sequence in the region of the G2019S mutation is aligned with orthologs from rat (XP_235581), mouse (AAH34074), frog (AAH76853), and puffer fish (CAG05593). The chromatogram shows the 6055G>A transition (G2019S)

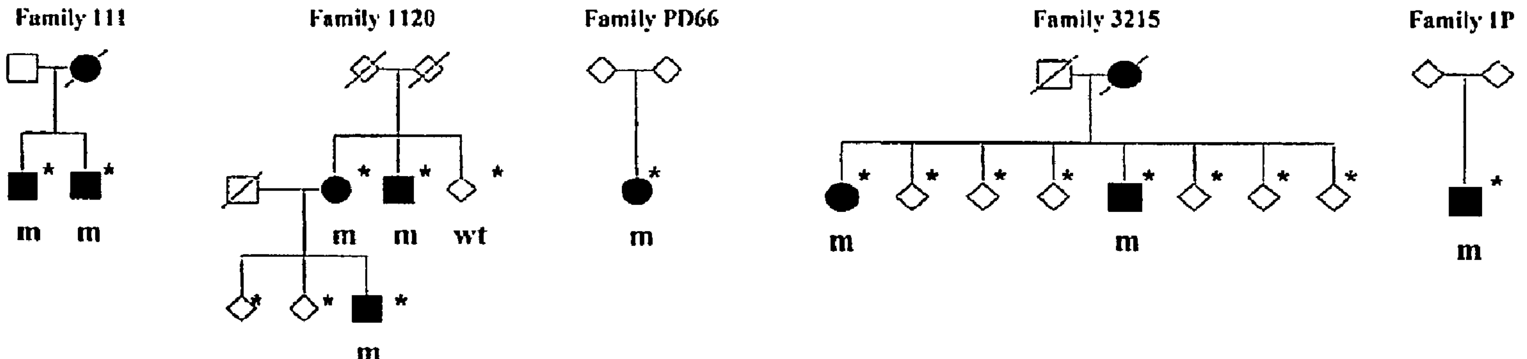

**Figure 2. Pedigrees of families with *LRRK2* G2019S**

□ and○ denotes sexes, and ◊ denotes that the sex is not given. A diagonal line across the symbol denotes that the person is dead, and thus that he/she has not been tested. Blackened symbols denote affected family members with parkinsonism. An asterisk denotes genotyped individual, with "m" for mutation carriers and "wt" for wild-type *LRRK2*. To protect confidentiality, the genotypes and genders of some unaffected individuals are not shown.

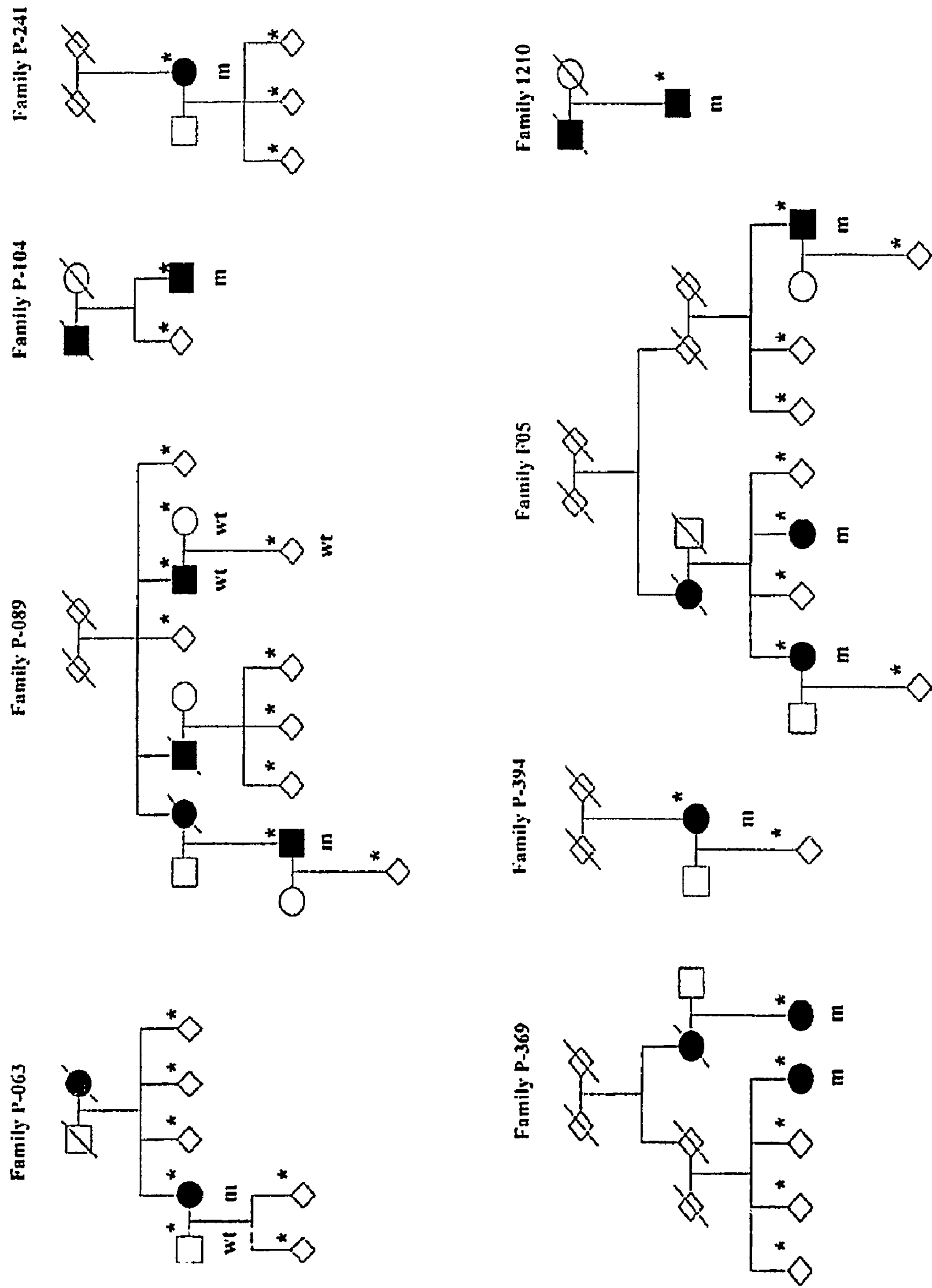
Figure 2, page 2

Figure 3. Chromosome 12q12 STR markers on the disease haplotype (PARK8).

| Marker | Family proband | | | | | | | | | | | | | |
|---|---|---|---|---|---|---|---|---|---|---|---|---|---|---|
| | P-063 | P-089 | P-104 | P-241 | P-369 | P-394 | F05 | 1210 | 1120 | 111 | 3215 | PD66 | 1P |
| D12S87 | 160 | 160 | 164 | 164 | - | 156 | 166 | 156/158 | 164 | 160 | 158 | 156/166 | 156/158 |
| D12S1648 | 120 | 120 | 122 | 122 | 122 | 110 | 110 | 122/124 | 110 | 110 | 110 | 120/134 | 128/130 |
| D12S2080 | 188 | 188 | 188 | 188 | 188 | 188 | 188 | 184/192 | 188 | 180 | 184 | 188/192 | 184/188 |
| D12S2194 | 265 | 265 | 265 | 265 | 265 | 265 | 261 | 253/261 | 257 | 257 | 253 | 245/249 | 249/261 |
| -31Kb | 290 | 290 | 290 | 290 | 290 | 290 | 290 | 290/290 | 290 | 290 | 290 | 290/293 | 284/290 |
| LRRK2_69Kb | 223 | 223 | 223 | 223 | 223 | 223 | 223 | 219/223 | 223 | 223 | 223 | 215/215 | 211/219 |
| LRRK2_84Kb | 253 | 253 | 253 | 253 | 253 | 253 | 253 | 253/253 | 253 | 253 | 253 | 253/253 | 253/253 |
| LRRK2_129Kb | 151 | 151 | 151 | 151 | 151 | 151 | 151 | 151/151 | 151 | 151 | 151 | 151/151 | 151/151 |
| 212Kb | 132 | 132 | 132 | 132 | 132 | 132 | 132 | 132/132 | 132 | 132 | 132/138 | 132/138 | 132/134 |
| 243Kb | 315 | 315 | 315 | 315 | 315 | 315 | 315 | 315/315 | 315 | 315 | 316/309 | 315/312 | 315/300 |
| 378Kb | 189 | 189 | 189 | 189 | 189 | 189 | 189 | 189/193 | 193 | 193 | 191 | 183/189 | 183/187 |
| D12S1048 | 214 | 214 | 214 | 214 | 214 | 211/214 | 214 | 214/223 | 214 | 214 | 223 | 211/214 | 211/226 |
| D12S1301 | 112 | 116 | 120 | 120 | 116 | 116 | 116 | 108/116 | 100 | 120 | 116 | 100/116 | 100/100 |
| D12S1701 | 95 | 97 | 91 | 91 | 95 | 95/97 | 97 | 95/101 | 92 | 91/95 | 95 | 97/101 | 91/97 |
| Country of origin | Norway | | | | | | | United States | | | Ireland | | Poland |

Genotypes for probands from13 families with *LRRK2* G2019S are shown, those shared are highlighted in grey.

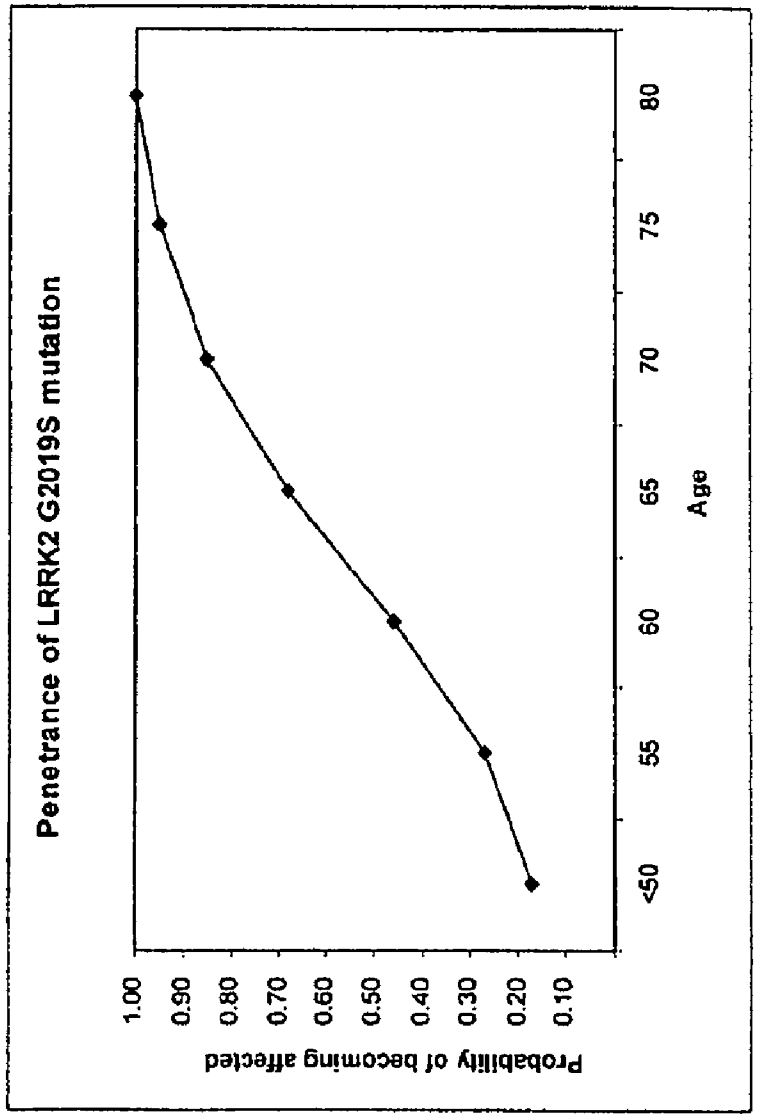
Figure 4. Probability of becoming affected by parkinsonism, in *LRRK2*G2019S carriers, as a function of age.

| | |
|---|---|
| LRRK2 | DYGIAQ----YCCRMGIKTSEGTPGFRAPE |
| LRRK1 | DYGISR----QSFHEGALGVEGTPGYQAPE |
| MATK | DFGLAK-----AERKGLDSSRLPVKWTAPE |
| PDGFRA | DFGLARDIMHDSNYVSKGSTFLPVKWMAPE |
| MAP3K10 | DFGLAR----EWHKTTKMSAAGTYAWMAPE |
| DAPK1 | DFGN-----------EFKNIFGTPEFVAPE |
| BRAF | DFGLATVKSRWSGSHQFEQLSGSILWMAPE |

Figure 5. Aligned amino acid sequences of the activation loop of different human kinases.

In most kinases, the activation loop starts and ends with the conserved residues DFG and APE, respectively . In *LRRK2* and *LRRK1* phenylalanine is changed to tyrosine, an amino acid with a similar structure. (LRRK2 – leucine-rich repeat kinase 2, LRRK1 – leucine-rich repeat kinase 1, MATK – megakaryocyte-associated tyrosine kinase, PDGFRA – platelet-derived growth factor receptor alpha, MAP3K10 – mitogen-activated protein kinase kinase kinase 10, DAPK1 – death-associated protein kinase 1, BRAF – v-raf murine sarcoma viral oncogene homolog B1)

POLYNUCLEOTIDE

This is a 371 of PCT/N02005/00465, filed Dec. 19, 2005.

Present invention relates to a novel polynucleotide involved in heritable Parkinson's disease (PD), a novel polypeptide encoded by the polynucleotide, and a method for diagnosing heritable Parkinson's disease (PD).

BACKGROUND

Parkinsonism (MIM168600) is a clinical syndrome characterized by bradykinesia, resting tremor, muscle rigidity, and postural instability (Gelb et al. 1999). The most common cause of parkinsonism is Parkinson's disease (PD). Second to Alzheimer's disease, PD is the most common neurodegenerative disorder affecting >1% of the population over 55 years of age (de Rijk et al. 1995). Neuropathological findings in PD are loss of pigmented neurons in the brainstem, substantia nigra and locus ceruleus, with intracellular Lewy body inclusions found within surviving neurons (Forno 1996).

Although PD is considered a sporadic disease, various hereditary forms of parkinsonism have been recognized (Vila and Przedborski 2004). A major breakthrough in recent years has been the mapping and cloning of a number of genes causing monogenic forms of parkinsonism. Genomic multiplication and missense mutations in the α-synuclein gene were initially identified in a small number of families with autosomal dominant parkinsonism (PARK1/4 [MIM 168601]) (Polymeropoulos et al. 1997; Kruger et al. 1998; Singleton et al. 2003; Chartier-Harlin et al. 2004; Farrer et al. 2004; Zarranz et al. 2004). Subsequently, α-synuclein antibodies were found to robustly stain Lewy bodies and Lewy neurites in the substantia nigra in familial and sporadic PD (Spillantini et al. 1997) and common genetic variability in the α-synuclein promoter has been implicated in sporadic PD (Pals et al. 2004).

Autosomal recessive mutations in three genes, parkin, DJ-1 and PINK1 have been linked with early-onset parkinsonism (<45 years at onset) (PARK2, PARK6 & PARK7 [MIM 602533, 602544 & 608309]) (Kitada et al. 1998; Bonifati et al. 2003; Valente et al. 2004). A large number of pathogenic mutations and rearrangements have been identified in the parkin gene reviewed by (Mata et al. 2004), but mutations in DJ-1 and PINK-1 are rare (unpublished data).

Very recently, five pathogenic mutations were identified in a gene, leucine-rich repeat kinase 2 (LRRK2) in six families with autosomal-dominant parkinsonism, linked to the PARK8 locus [MIM 607060]) (Zimprich et al. 2004a). Paisan-Ruiz and colleagues independently confirmed these findings of two pathogenic mutations in a British and Basque families (Paisan-Ruiz et al. x2004).

OBJECT

The object of the invention is to isolate a gene or polynucleotide proving inheritable parkinsonism, and to use presence of this gene to diagnose a patient before he/her gets sick. A further object is to use this gene or polynucleotide to transfect a microorganism or experimental animal in order to develop a new medicine for treating or preventing the onset of parkinsonism.

THE INVENTION

Inheritable parkinsonism may be proved by the method according to the characterizing part of claim 5, and the other objects are met by a polynucleotid according to the characterizing part of claim 1, a recombinant vector according to claim 3, a DNA probe and a DNA primer according to claims 4 and 6 respectively, and a peptide according to claim 9.

The inventors have isolated a novel LRRK2 mutation, and this mutation may cause development of dominantly inherited PD. By screening healthy persons, one can state whether the healthy persons have the mutation, and thus most likely will develop the illness.

Using a probe to test whether a patient has the mutation allows a precise, differential diagnosis of this type of Parkinson's disease. The probe represents a safe and accurate biomarker which will be powerful as it nominates subjects, future patients, for neuroprotective therapy. At the present time this is a research enterprise, but not for long. These subjects provide the first (and only) 'uniform substrate/background' for studies on drug efficacy/safety. From a research perspective they will also facilitate models of disease (*C. elegans, Drosophila,* mice) and epidemiological research on the variable expressivity and age-associated penetrance. As the sequence of the mutated gene is known, microorganisms and further experimental animals may be transfected, in order to investigate for a new medicine to treat or prevent the onset of the illness.

The genetic information provides subjects with the cause of their disease, an explanation for which, if handled correctly, can be of great psychological benefit (fulfilling the 'need to know' why). This information also prioritizes the resources of the research community, grant funding agencies and the pharmaceutical industry on developing a neuroprotective therapies to halt G2019S disease progression.

In the following the invention will be described by reference to a study of PD patients and their families. Parts of the study are shown in figures, wherein FIG. 1 shows a schematic drawing of LRRK2 with predicted protein domains, FIG. 2 shows pedigrees of families with LRRK2 G2019S, FIG. 3 shows chromosome 12q12 STR markers on the disease haplotype (PARK 8), FIG. 4 shows probability of becoming affected by parkinsonism, in LRRK2 G2019S carriers, as a function of age, and FIG. 5 shows aligned amino acid sequences of the activation ioop of different human kinases: LRRK2 (SEQ ID NO:17), LRRK1 (SEQ ID NO:18), MATK (SEQ ID NO:19), PDGFRA (SEQ ID NO:20), MAP3K10 (SEQ ID NO:21), DAPK1 (SEQ ID NO:22), and BRAF (SEQ ID NO:23).

The inventors identified seven unrelated persons all having the new mutation, from 248 multiplex kindreds with dominantly inherited PD, and six further unrelated persons from three populaton-based series of persons with dominantly inhereted PD. These 13 persons and their families made basis for the inventors' further work. Segregation and linkage analysis provides evidence for pathogenicity and an estimate of age-associated penetrance; haplotype analysis demonstrates the mutation originates from a common and ancient founder.

Subjects and Methods

Study Subjects

The patients and controls were examined by neurologists specialized in movement disorders. A full history, including family history and neurological examination, was completed on each patient. Clinical diagnosis of PD required the presence of at least two of three cardinal signs (resting tremor, bradykinesia and rigidity), improvement from adequate dopaminergic therapy and the absence of atypical features or other causes of parkinsonism.

LRRK2 Sequencing and Mutation Screening

Blood samples were taken and genomic DNA was extracted using standard techniques. Six families (families 194, 281, 3081, 3082, 3083 and 3211) were known to have a positive LOD-score for STR (Short Tandem Repeat) markers in the PARK8 locus (Zimprich et al. 2004b). Amplification of all 51 exons of the LRRK2 gene was performed by polymerase chain reaction (PCR) in one patient having PD, from each of these six families. All PCRs were carried out for each primer set with 20-50 ng of template DNA in a total volume of 25 μl using a final reaction concentration of 200 μM dNTP, 1×PCR-Buffer (Qiagen), 1×Q-Solution (Qiagen), and 0.8 μM of each primer. One unit of Taq polymerase (Qiagen) was added to each reaction. Amplification was performed using a 57-52° C.-touchdown protocol over 38 cycles. The primers used for PCR amplification of LRRK2 exons and for sequencing are available on request.

The nucleotide sequences of all PCR products were determined by direct sequencing. Each PCR product was cleaned by using a Millipore PCR purification plate. Three microliters of purified PCR product was used per sequencing reaction with 1 μl of either the forward or reverse PCR primer and 1 μl of BigDye reaction mix (Applied Biosystems). Electrophoresis was performed under standard conditions on an ABI 3730 automated sequencer (Applied Biosystems). All sequences were obtained with both forward and reverse primers. Sequences were analyzed with SeqScape software version 2.1.1 (Applied Biosystems) and compared with published sequence of LRRK2 (GenBank accession no. AY792511).

American, 550 Norwegian, 330 Irish and 180 Polish subjects), the latter to be used as control samples. Mutations were confirmed by direct sequencing of PCR products from LRRK2 exon 41. Finally, all participating family members of LRRK2 G2019 mutation carriers (affected and unaffected) were screened for the mutation.

By 6055 G>A or G6055A it is meant that nucleotide number 6055 of the LRRK2 gene, counted from the 5'end of the polynucleotide, has changed from G (guanine) to A (adenine). This change also causes a change in the polypeptide encoded by the polynucleotide, and G2019S denotes a polynucleotide where aminoacid number 2019 is changed from G (Glycine) to S (Serine). These shortenings are wellknown to persons skilled of the art.

Genotyping of STR Markers

Fourteen STR markers were genotyped in mutation carriers and all available family members, in all 13 families, for linkage analyses and to determine whether there was a particular haplotype associated with the LRRK2 mutation. STR markers were chosen to span the PARK8 region including D12S87, D12S1648, D12S2080, D12S2194, D12S1048, D12S1301 and D12S1701. LRRK2 is located between D12S2194 and D12S1048. We also developed seven novel STR markers in this region (shown in table 1 below) by searching for repeat polymorphisms using RepeatMasker of in silico BAC sequence (UCSC Human Genome Browser Web site). The labeling of these novel markers reflects their physical position relative to the start codon of LRRK2.

TABLE 1

Novel chromosome 12 STR markers

| Marker name | Primer sequence | Physical position (bp) On chromosome 12 | SEQ ID NO: |
|---|---|---|---|
| D12S2514 | F: 5'-TTGCAGCTGTAAGGAATTTGGG-3' | 38873779 | 3 |
| | R: 5'-GCATTCTTCAGCCTGAGACCC-3' | | 4 |
| D12S2515 | F: 5'-TGAAGGACACTGAACAAGATGG-3' | 38974140 | 5 |
| | R: 5'-GCCATAGTCCTTCCATAGTTCC-3' | | 6 |
| D12S2516 | F: 5'-CGCAGCGAGCATTGTACC-3' | 38989214 | 7 |
| | R: 5'-CTCGGAAAGTTTCCCAATTC-3' | | 8 |
| D12S2518 | F: 5'-CTGGTATTACCTCAACTGTGGCTC-3' | 39034800 | 9 |
| | R: 5'-ACTGGTATGTTTAAGCCTGGCAC-3' | | 10 |
| D12S2519 | F: 5'-AGCAGCAGAGAAGATTTCAATAAC-3' | 39116816 | 11 |
| | R: 5'-AATCATCTTTGAAAGAACCAGG-3' | | 12 |
| D12S2523 | F: 5'-TAAACGAAGCTCCCTCACTGTAAG-3' | 39147728 | 13 |
| | R: 5'-TCTTTGTAGCTGCGGTTGTTTC-3' | | 14 |
| D12S2517 | F: 5'-TCATGAAGATGTCTGTGATAGGGC-3' | 39282976 | 15 |
| | R: 5'-CTCTATTGTGAGCAAACTGCATGG-3' | | 16 |

After identification of a heterozygous G2019S (G6055A) mutation in the proband of family 3215 (referred to as family 3211 in Zimprich et al, 2004b), we designed a probe employing TaqMan chemistry on an ABI7900 (Applied Biosystems) to screen for this mutation. First we examined 248 PD patients from families with a known family history, consistent with autosomal dominant transmission of a suspected causative gene. Then 377 Norwegian, 271 Irish and 100 Polish PD patients (constituting the three population series) were checked using this assay; and 2260 samples of healthy persons from similar populations were also included (1200 US One primer of each pair was labeled with a fluorescent tag. PCR reactions were carried out on 10-20 ng of DNA in a total volume of 15 μl with final reaction concentrations of 150 μM dNTP, 1×PCR-Buffer (Qiagen), 1×Q-Solution (Qiagen) and 0.6 μM of each primer, with 1 unit of Taq Polymerase (Qiagen). Amplification was performed using a 57-52° C.-touchdown protocol over 38 cycles. The PCR product for each marker was diluted by a factor of 10 to 100 with water. One microliter was then added to 10 μl of Hi-Di Formamide and Rox size standard. All samples were run on an ABI 3100 genetic analyzer, and results were analyzed using Genescan 3.7 and Genotyper 3.7 software (Applied Biosystems). Since population allele frequencies were not available from the CEPH database, these have been estimated by genotyping 95 unrelated Caucasian subjects, a population based series from the United States (shown in table 2 below).

TABLE 2

| Allele frequencies of Park 8 Markers | |
|---|---|
| Marker and allele (bp) | Frequency (%) |
| D12S87 (n = 92) | |
| 150 | 0.5 |
| 154 | 1.1 |
| 156 | 27.2 |
| 158 | 33.2 |
| 160 | 11.4 |
| 162 | 2.7 |
| 164 | 6.0 |
| 166 | 17.4 |
| 168 | 0.5 |
| D12S1648 (n = 91) | |
| 110 | 13.7 |
| 112 | 3.3 |
| 114 | 11.0 |
| 116 | 4.4 |
| 118 | 2.2 |
| 120 | 2.8 |
| 122 | 17.0 |
| 124 | 3.9 |
| 126 | 7.7 |
| 128 | 14.3 |
| 130 | 8.8 |
| 132 | 2.8 |
| 134 | 2.8 |
| 136 | 1.7 |
| 138 | 0.6 |
| 140 | 2.2 |
| 142 | 1.1 |
| D12S2080 (n = 93) | |
| 176 | 1.6 |
| 180 | 20.2 |
| 184 | 44.7 |
| 188 | 22.9 |
| 192 | 10.6 |
| D12S2194 (n = 87) | |
| 245 | 0.6 |
| 249 | 40.9 |
| 253 | 32.4 |
| 257 | 19.9 |
| 261 | 4.6 |
| 265 | 1.7 |
| D12S2514 (n = 82) | |
| 284 | 11.0 |
| 291 | 53.1 |
| 294 | 32.3 |
| 297 | 1.2 |
| 300 | 2.4 |
| D12S2515 (n = 93) | |
| 208 | 3.2 |
| 212 | 26.6 |
| 216 | 18.6 |
| 220 | 22.9 |
| 224 | 20.7 |
| 228 | 5.3 |
| 232 | 2.7 |
| rs 7966550 (n = 90) | |
| T | 90.6 |
| C | 9.4 |

TABLE 2-continued

| Allele frequencies of Park 8 Markers | |
|---|---|
| Marker and allele (bp) | Frequency (%) |
| DS12S2516 | |
| 252 | 37.3 |
| 254 | 62.7 |
| rs 1427263 (n = 89) | |
| A | 63.6 |
| C | 36.5 |
| rs1116013 (n = 88) | |
| A | 49.4 |
| G | 50.6 |
| rs11564148 (n = 88) | |
| A | 26.1 |
| T | 73.9 |
| D12S2518 (N = 90) | |
| 154 | 79.7 |
| 168 | 15.9 |
| 170 | 4.4 |
| D12S519 (n = 72) | |
| 132 | 29.5 |
| 134 | 22.6 |
| 138 | 22.6 |
| 140 | 25.3 |
| D12S2520 (N = 85) | |
| 248 | 8.2 |
| 251 | 7.6 |
| 254 | 10.0 |
| 257 | 54.1 |
| 260 | 20.0 |
| D12S2521 (N = 93) | |
| 311 | 0.5 |
| 315 | 10.8 |
| 319 | 20.4 |
| 323 | 8.1 |
| 327 | 7.0 |
| 331 | 8.1 |
| 335 | 0.5 |
| 355 | 1.1 |
| 359 | 7.5 |
| 363 | 13.4 |
| 367 | 7.0 |
| 371 | 7.0 |
| 375 | 6.5 |
| 379 | 3.8 |
| 383 | 1.1 |
| 387 | .5 |
| D12S2522 (N = 93) | |
| 281 | 9.1 |
| 283 | 14.0 |
| 285 | .5 |
| 287 | 11.3 |
| 293 | .5 |
| 295 | 15.6 |
| 297 | 44.6 |
| 299 | 4.3 |
| D12S2523 (n = 89) | |
| 305 | 18.9 |
| 314 | 41.1 |
| 317 | 8.9 |
| 320 | 30.0 |
| 323 | 1.1 |
| D12S2517 (n = 93) | |
| 180 | 8.5 |
| 182 | 7.5 |
| 184 | 15.4 |
| 186 | 8.5 |

TABLE 2-continued

Allele frequencies of Park 8 Markers

| Marker and allele (bp) | Frequency (%) |
|---|---|
| 188 | 11.7 |
| 190 | 8.0 |
| 192 | 5.3 |
| 194 | 1.1 |
| 196 | 1.1 |
| 198 | 3.2 |
| 200 | 0.5 |
| 202 | 3.7 |
| 204 | 6.9 |
| 206 | 6.9 |
| 208 | 4.3 |
| 210 | 2.1 |
| 212 | 3.2 |
| 214 | 1.6 |
| 216 | 0.5 |
| D12S1048 (n = 89) | |
| 211 | 37.2 |
| 214 | 21.1 |
| 217 | 17.8 |
| 220 | 2.2 |
| 223 | 6.7 |
| 226 | 11.7 |
| 229 | 3.3 |
| D12S1301 (n = 93) | |
| 96 | 0.5 |
| 100 | 37.2 |
| 104 | 17.6 |
| 108 | 11.1 |
| 112 | 12.2 |
| 116 | 13.3 |
| 120 | 7.5 |
| 124 | 0.5 |
| D12S1701 (n = 93) | |
| 89 | 4.3 |
| 91 | 4.8 |
| 93 | 10.8 |
| 95 | 40.0 |
| 97 | 16.0 |
| 99 | 12.4 |
| 101 | 11.8 |
| 103 | 0.5 |

A The number of individuals genotyped is given for each marker (n)
B Alle frequencies are for individual markers in U.S. control subjects Statistical Analysis Multipoint nonparametric LOD scores for all families were calculated using GENEHUNTER-PLUS (Kong and Cox 1997). The frequency of the deleterious allele was set at 0.0001, and empirically determined allele frequencies were employed. The map positions for each marker were taken from Rutgers combined linkage-physical map version 1.0 (MAP-O-MAT web site). The three loci D12S2080, D12S2194 and D12S1301 are very tightly linked, with no observed recombinants in the database or within our genotyped families, and thus inter-marker distances were assigned as 0.01 cM.

Chromosome 12 haplotypes in the PARK8 region were established for those families in which chromosome phase for mutation-carrying individuals could be deduced, thereby determining which alleles co-segregated with the LRRK2 G2019S mutation in each family. For those affected individuals in whom the associated allele for a marker could not be determined, both alleles are given.

The age-dependent penetrance was estimated as the probability of a gene carrier becoming affected, at a given age, within the 13 families. The number of affected mutation carriers, for each decade, was divided by the total number of affected individuals, plus the number of unaffected carriers within that range. For some affected family members no DNA was available and only historical data on the disease course was obtained. These individuals were excluded from penetrance calculations.

Results

As mentioned previously, we identified 13 affected probands (i.e. 13 patients) who carry a heterozygous G6055A mutation in exon 41 of the LRRK2 gene. The mutation leads to a G2019S amino acid substitution of a highly conserved residue within the predicted activation loop of the MAPKKK (Mitogen-Activated Protein Kinase Kinase Kinase) domain (FIG. 1). After genotyping a total of 42 additional family members, 22 additional subjects were found to carry the mutation, seven with a diagnosis of PD (shown in table 3 below). One affected member of family P-089 did not carry the mutation and, for the purposes of this study, was considered a phenocopy and excluded from further analyses. Seven families originated from Norway, three were from the United States, two from Ireland, and one was from Poland. One family from the United States descended from Russian/Rumania, and another from Italy. For only one family (family 111), the ethnic origin was unknown. The LRRK2 G2019S mutation segregates with disease in all kindreds, consistent with autosomal dominant transmission. To ensure patient confidentiality, simplified versions of the family pedigrees are presented in FIG. 2. There was no evidence of the mutation in the 2260 control samples.

Age at onset of clinical symptoms was quite variable, even within the same family. Family 1120, a family from the United States, had both the earliest and latest age at onset for a patient. The youngest affected subject had an onset at 39 years, whereas the oldest carrier presented with initial symptoms at 78 years. Where recorded, most LRRK2 G2019S carriers have late-onset disease (>50 years at onset). The mean age at onset of affected mutation carriers was 56.8 years (range 39-78 years, n=19). Unaffected carriers have a mean age of 53.9 years (range 26-74 years, n=14). The penetrance of the mutation was found to be highly age-dependent, increasing from 17% at the age of 50 to 85% at the age of 70 (FIG. 4).

TABLE 3

Demographic and Clinical Information for 13 Families with LRRK2 G2019S

| | FINDINGS FOR FAMILY | | | | | | | | | | | | |
|---|---|---|---|---|---|---|---|---|---|---|---|---|---|
| CHARACTERISTIC | P-063 | P-089 | P-104 | P-241 | P-369 | P-394 | F05 | 1210 | 111 | 1120 | PD66 | 3211 | IP |
| Country of origin | Norway | Norway | Norway | Norway | Norway | Norway | Norway | United States | United States | United States | Ireland | Ireland | Poland |
| No. of generations | 3 | 4 | 3 | 3 | 3 | 4 | 4 | 2 | 2 | 3 | 1 | 2 | 1 |
| No. of affected individuals | 2 | 4 | 4 | 1 | 3 | 4 | 5 | 2 | 3 | 3 | 1 | 3 | 1 |

TABLE 3-continued

Demographic and Clinical Information for 13 Families with LRRK2 G2019S

| CHARACTERISTIC | FINDINGS FOR FAMILY | | | | | | | | | | | | |
|---|---|---|---|---|---|---|---|---|---|---|---|---|---|
| | P-063 | P-089 | P-104 | P-241 | P-369 | P-394 | F05 | 1210 | 111 | 1120 | PD66 | 3211 | IP |
| No. of typed individuals affected (unaffected) | 1 (6) | 2 (8) | 1 (1) | 1 (4) | 2 (3) | 1 (1) | 3 (6) | 1 (0) | 2 (0) | 3 (3) | 1 (0) | 2 (6) | 1 (0) |
| No. of typed generations | 2 | 3 | 1 | 2 | 1 | 2 | 2 | 1 | 1 | 2 | 1 | 1 | 1 |
| Age[a] at onset in years (range) | 59 (53-65) | 59 (43-70) | 58 | 60 | 50 (43-61) | 66 | 64 (61-70) | 65 | 58 (57-58) | 59 (39-78) | 41 | 46 (40-52) | 73 |
| Maximum mLOD score | 0 | .30 | 0 | 0 | .60 | 0 | .90 | 0 | .09 | .30 | 0 | .30 | 0 |

[a]Average ages at onset are given when affected individuals. n ≧ 2

Evidence for linkage (the statistical burden of proof that this mutation causes disease) to the PARK8 locus was found across families, combined maximum multipoint LOD score of 2.41 [for all 14 markers], corresponding to a P value of $4.3\times10^{-4}$. As region was investigated, rather than a genome-wide search, this LOD score exceeds that required for significance, P=0.01 (Lander and K 1995). A positive LOD score was found in all families where more then one affected subject was genotyped (table 3).

All affected members from the different families, except the individual in family P-089 who did not carry the mutation, appear to share a common haplotype on chromosome 12 the LRRK2 gene locus (FIG. 3). Haplotypes can be established with certainty in nine of the families, and all mutation carriers in these families share alleles for four STR markers and 4 single nucleotide polymorphisms (SNPs) in the LRRK2 gene locus. These markers are LRRK2 D12S2516, D12S2518, D12S2519, D12S2520 and SNPs rs7966550, rs1427263, rs11176013, rs11564148. For the remaining families, the number of available samples from relatives was not sufficient to determine phase. However, the genotypes in these cases are consistent with a common LRRK2 G2019S allele. D12S2516 is located in intron 29 and D12S2518 is located in intron 44 of the LRRK2 gene, whereas the two other shared markers are positioned 3' of the gene. Using the physical position of the shared and non-shared markers, the size of the shared haplotype is between 145 kb and 154 kb.

Discussion

We have identified a novel LRRK2 mutation, G2019S, which co-segregates with autosomal dominant parkinsonism in 13 kindreds originating from several European populations. Positive LOD scores were obtained in multiplex families, and combined they provide significant support for the PARK8 locus. LRRK2 G2019S mutation was absent in a large number of control subjects, and of similar ethnicity. The number of families linked to LRRK2 in this and previous studies now explains the majority of genetically defined autosomal dominant parkinsonism.

The mean age at onset of affected LRRK2 G2019S carriers was 56.8 years, and comparable to that of patients in other families linked to PARK8 (Funayama et al. 2002; Paisan-Ruiz et al. 2004; Zimprich et al. 2004a). The majority of patients present with late-onset disease, indistinguishable from typical idiopathic PD. Disease penetrance is age-dependent, and increases in a linear fashion from 17% at the age of 50 to 85% at the age of 70. Age is the single most consistent risk factor for development of PD and other neurodegenerative disorders (Lang and Lozano 1998), and an important risk factor in LRRK2 associated parkinsonism. Interestingly, age at onset was variable in this study, both within and between different families, suggesting other susceptibility factors, environmental or genetic, may influence the phenotype.

Although our findings clearly indicate that LRRK2 mutations account for a substantial proportion of familial late-onset parkinsonism, historically, cross-sectional twin studies have not supported a genetic etiology for late-onset PD (Tanner et al. 1999; Wirdefeldt et al. 2004). The age-associated penetrance of LRRK2 mutations provides some explanation as even large and well designed twin studies are underpowered to detect incompletely penetrant mutations (Simon et al. 2002). LRRK2 mutations were also found in apparently sporadic PD patients; three of the patients in this study did not have any known affected first- or second-degree relatives. However, a caveat of age-dependent penetrance is that carriers may die of other diseases, before manifesting or being diagnosed with PD. Thus, it seems difficult to separate sporadic and familial PD, or to hypothesize environmental causes to be more important in one group and genetic causes more prominent in the other. In light of these results, a family history of parkinsonism, previously considered an exclusion criterion for a diagnosis of PD, must be reconsidered (Hughes et al. 1992).

LRRK2 is a member of the recently defined ROCO protein family (Bosgraaf and Van Haastert 2003). In human, mouse and rat, members of the ROCO protein family have five conserved domains (FIG. 1). The kinase domain belongs to the MAPKKK subfamily of kinases. The active sites of all kinases are located in a cleft between an N-terminal and a C-terminal lobe, typically covered by an 'activation loop', in an inactive conformation. The activation loop must undergo crucial structural changes to allow access to peptide substrates and to orientate key catalytic amino acids (Huse and Kuriyan 2002). In different kinases, the activation loop starts and ends with the conserved residues asp-phe-gly (DFG) and ala-pro-glu (APE), respectively (Dibb et al. 2004). Of note, the LRRK2 G2019S substitution changes a highly conserved amino acid at the start of this loop (FIG. 5). In a German family we previously described, an I2020T mutation is located in an adjacent codon (Zimprich et al. 2004a). In other kinases, oncogenic mutations in residues within the activation loop of the kinase domain have an activating effect (Davies et al. 2002), thus we postulate LRRK2 G2019S and I 2020T mutations may have an effect on its kinase activity.

The age of an allele may be estimated from the genetic variation among different copies (intra-allelic variation), or from its frequency (Slatkin and Rannala 2000). However, the local recombination rate on chromosome 12q12 is unknown, as is the frequency of the G2019S mutation in the general population. Nevertheless, at centromeres there is generally a dearth in recombination; indeed no crossovers have been observed between LRRK2 flanking markers D12S2194 and D12S1048 in our studies, or within CEPH families (MAP-O-MAT web site). The physical size of the shared haplotype is also small, between 145 kb and 154 kb, and the allele is widespread in families from several European populations. Hence, the mutation is likely to be ancient and may be relatively common in specific populations. These data suggest a substantial proportion of late-onset PD will have a genetic basis.

Electronic-Database Information

The physical position of markers is from NCBI build 34. Accession numbers and URLs for data presented herein are as follows:

Online Mendelian Inheritance in Man (OMIM), http://www.ncbi.nlm.nih.gov/Omim/

MAP-O-MAT, http://compgen.rutgers.edu/mapomat

RepeatMasker, http://www.repeatmasker.org/

REFERENCES

Bonifati V, Rizzu P, van Baren M J, Schaap O, Breedveld G J, Krieger E, Dekker M C, Squitieri F, Ibanez P, Joosse M, van Dongen J W, Vanacore N, van Swieten J C, Brice A, Meco G, van Duijn C M, Oostra B A, Heutink P (2003) Mutations in the DJ-1 gene associated with autosomal recessive early-onset parkinsonism. Science 299:256-9

Bosgraaf L, Van Haastert P J (2003) Roc, a Ras/GTPase domain in complex proteins. Biochim Biophys Acta 1643:5-10

Chartier-Harlin M C, Kachergus J, Roumier C, Mouroux V, Douay X, Lincoln S, Levecque C, Larvor L, Andrieux J, Hulihan M, Waucquier N, Defebvre L, Amouyel P, Farrer M, Destee A (2004) Alpha-synuclein locus duplication as a cause of familial Parkinson's disease. Lancet 364:1167-9

Davies H, Bignell G R, Cox C, Stephens P, Edkins S, Clegg S, Teague J, et al. (2002) Mutations of the BRAF gene in human cancer. Nature 417:949-54 de Rijk M C, Breteler M M, Graveland G A, Ott A, Grobbee D E, van der Meche F G, Hofman A (1995) Prevalence of Parkinson's disease in the elderly: the Rotterdam Study. Neurology 45:2143-6

Dibb N J, Dilworth S M, Mol C D (2004) Switching on kinases: oncogenic activation of BRAF and the PDGFR family. Nat Rev Cancer 4:718-27

Farrer M, Kachergus J, Forno L, Lincoln S, Wang D S, Hulihan M, Maraganore D, Gwinn-Hardy K, Wszolek Z, Dickson D, Langston J W (2004) Comparison of kindreds with parkinsonism and alpha-synuclein genomic multiplications. Ann Neurol 55:174-9

Forno L S (1996) Neuropathology of Parkinson's disease. J Neuropathol Exp Neurol 55:259-72

Funayama M, Hasegawa K, Kowa H, Saito M, Tsuji S, Obata F (2002) A new locus for Parkinson's disease (PARK8) maps to chromosome 12p11.2-q13.1. Ann Neurol 51:296-301

Gelb D J, Oliver E, Gilman S (1999) Diagnostic criteria for Parkinson disease. Arch Neurol 56:33-9

Hughes A J, Daniel S E, Kilford L, Lees A J (1992) Accuracy of clinical diagnosis of idiopathic Parkinson's disease: a clinico-pathological study of 100 cases. J Neurol Neurosurg Psychiatry 55:181-4

Huse M, Kuriyan J (2002) The conformational plasticity of protein kinases. Cell 109:275-82

Kitada T, Asakawa S, Hattori N, Matsumine H, Yamamura Y, Minoshima S, Yokochi M, Mizuno Y, Shimizu N (1998) Mutations in the parkin gene cause autosomal recessive juvenile parkinsonism. Nature 392:605-8

Kong A, Cox N J (1997) Allele-sharing models: LOD scores and accurate linkage tests. Am J Hum Genet 61:1179-88

Kruger R, Kuhn W, Muller T, Woitalla D, Graeber M, Kosel S, Przuntek H, Epplen J T, Schols L, Riess O (1998) Ala30Pro mutation in the gene encoding alpha-synuclein in Parkinson's disease. Nat Genet 18:106-8

Lander E, Kruglyak L (1995) Genetic dissection of complex traits: guidelines for interpreting and reporting linkage results. Nat Genet 1:241-7

Lang A E, Lozano A M (1998) Parkinson's disease. First of two parts. N Engl J Med 339:1044-53

Mata I F. Lockhart P J, Farrer M J (2004) Parkin genetics: one model for Parkinson's disease. Hum Mol Genet 13 Spec No 1:R127-33

Paisan-Ruiz C, Jain S, Evans E W, Gilks W P, Simon J, van der Brug M, de Munain A L, Aparicio S, Gil A M, Khan N, Johnson J, Martinez J R, Nicholl D, Carrera I M, Pena A S, de Silva R, Lees A, Marti-Masso J F, Perez-Tur J, Wood N W, Singleton A B (2004) Cloning of the Gene Containing Mutations that Cause PARK8-Linked Parkinson's Disease. Neuron 44:595-600

Pals P, Lincoln S, Manning J, Heckman M, Skipper L, Hulihan M, Van den Broeck M, De Pooter T, Cras P, Crook J, Van Broeckhoven C, Farrer M J (2004) alpha-Synuclein promoter confers susceptibility to Parkinson's disease. Ann Neurol 56:591-5

Polymeropoulos M H, Lavedan C, Leroy E, Ide S E, Dehejia A, Dutra A, Pike B, Root H, Rubenstein J, Boyer R, Stenroos E S, Chandrasekharappa S, Athanassiadou A, Papapetropoulos T, Johnson W G, Lazzarini A M, Duvoisin R C, Di Iorio G, Golbe L I, Nussbaum R L (1997) Mutation in the alpha-synuclein gene identified in families with Parkinson's disease. Science 276:2045-7

Simon D K, Lin M T, Pascual-Leone A (2002) "Nature versus nurture" and incompletely penetrant mutations. J Neurol Neurosurg Psychiatry 72:686-9

Singleton A B, Farrer M, Johnson J, Singleton A, Hague S, Kachergus J, Hulihan M, Peuralinna T, Dutra A, Nussbaum R, Lincoln S, Crawley A, Hanson M, Maraganore D, Adler C, Cookson M R, Muenter M, Baptista M, Miller D, Blancato J, Hardy J, Gwinn-Hardy K (2003) alpha-Synuclein locus triplication causes Parkinson's disease. Science 302:841

Slatkin M, Rannala B (2000) Estimating allele age. Annu Rev Genomics Hum Genet 1:225-49

Spillantini M G, Schmidt M L, Lee V M, Trojanowski J Q, Jakes R, Goedert M (1997) Alpha-synuclein in Lewy bodies. Nature 388:839-40

Tanner C M, Ottman R, Goldman S M, Ellenberg J, Chan P, Mayeux R, Langston J W (1999) Parkinson disease in twins: an etiologic study. Jama 281:341-6

Valente E M, Abou-Sleiman P M, Caputo V, Muqit M M, Harvey K, Gispert S, Ali Z, Del Turco D, Bentivoglio A R, Healy D G, Albanese A, Nussbaum R, Gonzalez-Maldonado R, Deller T, Salvi S, Cortelli P, Gilks W P, Latchman D S, Harvey R J, Dallapiccola B, Auburger G. Wood N W (2004) Hereditary early-onset Parkinson's disease caused by mutations in PINK1. Science 304:1158-60

Vila M, Przedborski S (2004) Genetic clues to the pathogenesis of Parkinson's disease. Nat Med 10 Suppl:S58-62

Wirdefeldt K, Gatz M, Schalling M, Pedersen N L (2004) No evidence for heritability of Parkinson disease in Swedish twins. Neurology 63:305-11

Zarranz J J, Alegre J, Gomez-Esteban J C, Lezcano E, Ros R, Ampuero I, Vidal L, Hoenicka J, Rodriguez O, Atares B, Llorens V, Gomez Tortosa E, del Ser T, Munoz D G, de Yehenes J G (2004) The new mutation, E46K, of alpha-synuclein causes Parkinson and Lewy body dementia. Ann Neurol 55:164-73

Zimprich A, Biskup S, Leitner P, Lichtner P, Farrer M, Lincoln S, Kachergus J, Hulihan M, Uitti R J, Caine D B, Stoessl A J, Pfeiffer R F, Patenge N, Carbajal I C, Vieregge P, Asmus F, Muller-Myhsok B, Dickson D W, Meitinger T, Strom T M, Wszolek Z K, Gasser T (2004a) Mutations in LRRK2 Cause Autosomal-Dominant Parkinsonism with Pleomorphic Pathology. Neuron 44:601-7

Zimprich A, Muller-Myhsok B, Farrer M, Leitner P, Shanna M, Hulihan M, Lockhart P, Strongosky A, Kachergus J, Calne D B, Stoessl J, Uitti R J, Pfeiffer R F, Trenkwalder C, Homann N, Ott E, Wenzel K, Asmus F, Hardy J, Wszolek Z, Gasser T (2004b) The PARK8 locus in autosomal dominant parkinsonism: confirmation of linkage and further delineation of the disease-containing interval. Am J Hum Genet 74:11-9

The invention claimed is:

1. An isolated polynucleotide consisting of the base sequence of SEQ ID NO:2, or a complementary strand thereto, wherein the nucleotide at position 6055 of SEQ ID NO:2 is A, C or T.

2. A polynucleotide according to claim 1, wherein the polynucleotide is at least a part of a gene.

3. A recombinant vector comprising a polynucleotide according to claim 1.

4. An isolated polynucleotide containing more than 10 consecutive nucleotides from the SEQ ID NO:2 or the complementary strand thereof, wherein the polynucleotide contains nucleotide position 6055 of SEQ ID NO:2.

5. The polynucleotide of claim 4, wherein the nucleotide at the position corresponding to position 6055 of SEQ ID NO:2 is A.

* * * * *

UNITED STATES PATENT AND TRADEMARK OFFICE

CERTIFICATE OF CORRECTION

PATENT NO. : 7,544,786 B2
APPLICATION NO. : 10/568414
DATED : June 9, 2009
INVENTOR(S) : Aasly et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 11 days.

Delete the phrase "by 11 days" and insert -- by 0 days --

Signed and Sealed this

Twentieth Day of April, 2010

David J. Kappos
*Director of the United States Patent and Trademark Office*

SEQUENCE LISTING

```
<160> NUMBER OF SEQ ID NOS: 2

<210> SEQ ID NO 1
<211> LENGTH: 2527
<212> TYPE: PRT
<213> ORGANISM: Homo sapiens
<220> FEATURE:
<221> NAME/KEY: MISC_FEATURE
<222> LOCATION: (2019)..(2019)
<223> OTHER INFORMATION: X may be any amino acid except glycine.
<300> PUBLICATION INFORMATION:
<308> DATABASE ACCESSION NUMBER: Genbank / AY792511
<309> DATABASE ENTRY DATE: 2004-11-15
<313> RELEVANT RESIDUES: (1)..(2527)

<400> SEQUENCE: 1

Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
35                  40                  45

Glu His Ala Ser Lys Leu Phe Gln Gly Lys Asn Ile His Val Pro Leu
50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
        85                  90                  95

Gln Ser Leu Met Gly Pro Gln Asp Val Gly Asn Asp Trp Glu Val Leu
    100                 105                 110

Gly Val His Gln Leu Ile Leu Lys Met Leu Thr Val His Asn Ala Ser
115                 120                 125

Val Asn Leu Ser Val Ile Gly Leu Lys Thr Leu Asp Leu Leu Leu Thr
130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
        165                 170                 175

Gln Lys Leu Gly Cys Lys Ala Leu His Val Leu Phe Glu Arg Val Ser
    180                 185                 190

Glu Glu Gln Leu Thr Glu Phe Val Glu Asn Lys Asp Tyr Met Ile Leu
195                 200                 205

Leu Ser Ala Ser Thr Asn Phe Lys Asp Glu Glu Glu Ile Val Leu His
210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
        245                 250                 255
```

-continued

```
Met Lys Ala Phe Pro Met Ser Glu Arg Ile Gln Glu Val Ser Cys Cys
    260                 265                 270

Leu Leu His Arg Leu Thr Leu Gly Asn Phe Phe Asn Ile Leu Val Leu
275                 280                 285

Asn Glu Val His Glu Phe Val Val Lys Ala Val Gln Gln Tyr Pro Glu
290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
        325                 330                 335

Glu Asn Asp Asp Glu Gly Glu Glu Asp Lys Leu Phe Trp Leu Glu Ala
    340                 345                 350

Cys Tyr Lys Ala Leu Thr Trp His Arg Lys Asn Lys His Val Gln Glu
355                 360                 365

Ala Ala Cys Trp Ala Leu Asn Asn Leu Leu Met Tyr Gln Asn Ser Leu
370                 375                 380

His Glu Lys Ile Gly Asp Glu Asp Gly His Phe Pro Ala His Arg Glu
385                 390                 395                 400

Val Met Leu Ser Met Leu Met His Ser Ser Ser Lys Glu Val Phe Gln
        405                 410                 415

Ala Ser Ala Asn Ala Leu Ser Thr Leu Leu Glu Gln Asn Val Asn Phe
    420                 425                 430

Arg Lys Ile Leu Leu Ser Lys Gly Ile His Leu Asn Val Leu Glu Leu
435                 440                 445

Met Gln Lys His Ile His Ser Pro Glu Val Ala Glu Ser Gly Cys Lys
450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
        485                 490                 495

Ser Leu Pro Val Gln Leu Glu Ala Leu Arg Ala Ile Leu His Phe Ile
    500                 505                 510

Val Pro Gly Met Pro Glu Glu Ser Arg Glu Asp Thr Glu Phe His His
515                 520                 525

Lys Leu Asn Met Val Lys Lys Gln Cys Phe Lys Asn Asp Ile His Lys
530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
        565                 570                 575

Leu Glu Met Leu Ser Leu Glu Gly Ala Met Asp Ser Val Leu His Thr
    580                 585                 590

Leu Gln Met Tyr Pro Asp Asp Gln Glu Ile Gln Cys Leu Gly Leu Ser
595                 600                 605

Leu Ile Gly Tyr Leu Ile Thr Lys Lys Asn Val Phe Ile Gly Thr Gly
610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
        645                 650                 655

Lys Leu Ser Ala Ser Phe Ser Lys Leu Leu Val His His Ser Phe Asp
    660                 665                 670
```

-continued

```
Leu Val Ile Phe His Gln Met Ser Ser Asn Ile Met Glu Gln Lys Asp
675                 680                 685

Gln Gln Phe Leu Asn Leu Cys Cys Lys Cys Phe Ala Lys Val Ala Met
690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Leu Gly Ala Asp Ala Asn
        725                 730                 735

Gln Ala Lys Glu Gly Ser Ser Leu Ile Cys Gln Val Cys Glu Lys Glu
    740                 745                 750

Ser Ser Pro Lys Leu Val Glu Leu Leu Leu Asn Ser Gly Ser Arg Glu
755                 760                 765

Gln Asp Val Arg Lys Ala Leu Thr Ile Ser Ile Gly Lys Gly Asp Ser
770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
        805                 810                 815

Trp Leu Gly Pro Leu Phe Pro Asp Lys Thr Ser Asn Leu Arg Lys Gln
    820                 825                 830

Thr Asn Ile Ala Ser Thr Leu Ala Arg Met Val Ile Arg Tyr Gln Met
835                 840                 845

Lys Ser Ala Val Glu Glu Gly Thr Ala Ser Gly Ser Asp Gly Asn Phe
850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
        885                 890                 895

Gly Ser Glu Gly Ser Phe Leu Val Lys Lys Lys Ser Asn Ser Ile Ser
    900                 905                 910

Val Gly Glu Phe Tyr Arg Asp Ala Val Leu Gln Arg Cys Ser Pro Asn
915                 920                 925

Leu Gln Arg His Ser Asn Ser Leu Gly Pro Ile Phe Asp His Glu Asp
930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
        965                 970                 975

Leu Ala Ser Glu Arg Glu Tyr Ile Thr Ser Leu Asp Leu Ser Ala Asn
    980                 985                 990

Glu Leu Arg Asp Ile Asp Ala Leu  Ser Gln Lys Cys Cys  Ile Ser Val
995                 1000                1005

His Leu  Glu His Leu Glu Lys  Leu Glu Leu His Gln  Asn Ala Leu
1010                1015                1020

Thr Ser  Phe Pro Gln Gln Leu  Cys Glu Thr Leu Lys  Ser Leu Thr
1025                1030                1035

His Leu  Asp Leu His Ser Asn  Lys Phe Thr Ser Phe  Pro Ser Tyr
1040                1045                1050

Leu Leu  Lys Met Ser Cys Ile  Ala Asn Leu Asp Val  Ser Arg Asn
1055                1060                1065

Asp Ile  Gly Pro Ser Val Val  Leu Asp Pro Thr Val  Lys Cys Pro
1070                1075                1080

Thr Leu  Lys Gln Phe Asn Leu  Ser Tyr Asn Gln Leu  Ser Phe Val
```

-continued

```
1085                1090                1095

Pro Glu  Asn Leu Thr Asp Val  Val Glu Lys Leu Glu  Gln Leu Ile
1100                1105                1110

Leu Glu  Gly Asn Lys Ile Ser  Gly Ile Cys Ser Pro  Leu Arg Leu
1115                1120                1125

Lys Glu  Leu Lys Ile Leu Asn  Leu Ser Lys Asn His  Ile Ser Ser
1130                1135                1140

Leu Ser  Glu Asn Phe Leu Glu  Ala Cys Pro Lys Val  Glu Ser Phe
1145                1150                1155

Ser Ala  Arg Met Asn Phe Leu  Ala Ala Met Pro Phe  Leu Pro Pro
1160                1165                1170

Ser Met  Thr Ile Leu Lys Leu  Ser Gln Asn Lys Phe  Ser Cys Ile
1175                1180                1185

Pro Glu  Ala Ile Leu Asn Leu  Pro His Leu Arg Ser  Leu Asp Met
1190                1195                1200

Ser Ser  Asn Asp Ile Gln Tyr  Leu Pro Gly Pro Ala  His Trp Lys
1205                1210                1215

Ser Leu  Asn Leu Arg Glu Leu  Leu Phe Ser His Asn  Gln Ile Ser
1220                1225                1230

Ile Leu  Asp Leu Ser Glu Lys  Ala Tyr Leu Trp Ser  Arg Val Glu
1235                1240                1245

Lys Leu  His Leu Ser His Asn  Lys Leu Lys Glu Ile  Pro Pro Glu
1250                1255                1260

Ile Gly  Cys Leu Glu Asn Leu  Thr Ser Leu Asp Val  Ser Tyr Asn
1265                1270                1275

Leu Glu  Leu Arg Ser Phe Pro  Asn Glu Met Gly Lys  Leu Ser Lys
1280                1285                1290

Ile Trp  Asp Leu Pro Leu Asp  Glu Leu His Leu Asn  Phe Asp Phe
1295                1300                1305

Lys His  Ile Gly Cys Lys Ala  Lys Asp Ile Ile Arg  Phe Leu Gln
1310                1315                1320

Gln Arg  Leu Lys Lys Ala Val  Pro Tyr Asn Arg Met  Lys Leu Met
1325                1330                1335

Ile Val  Gly Asn Thr Gly Ser  Gly Lys Thr Thr Leu  Leu Gln Gln
1340                1345                1350

Leu Met  Lys Thr Lys Lys Ser  Asp Leu Gly Met Gln  Ser Ala Thr
1355                1360                1365

Val Gly  Ile Asp Val Lys Asp  Trp Pro Ile Gln Ile  Arg Asp Lys
1370                1375                1380

Arg Lys  Arg Asp Leu Val Leu  Asn Val Trp Asp Phe  Ala Gly Arg
1385                1390                1395

Glu Glu  Phe Tyr Ser Thr His  Pro His Phe Met Thr  Gln Arg Ala
1400                1405                1410

Leu Tyr  Leu Ala Val Tyr Asp  Leu Ser Lys Gly Gln  Ala Glu Val
1415                1420                1425

Asp Ala  Met Lys Pro Trp Leu  Phe Asn Ile Lys Ala  Arg Ala Ser
1430                1435                1440

Ser Ser  Pro Val Ile Leu Val  Gly Thr His Leu Asp  Val Ser Asp
1445                1450                1455

Glu Lys  Gln Arg Lys Ala Cys  Met Ser Lys Ile Thr  Lys Glu Leu
1460                1465                1470

Leu Asn  Lys Arg Gly Phe Pro  Ala Ile Arg Asp Tyr  His Phe Val
1475                1480                1485
```

-continued

```
Asn Ala  Thr Glu Glu Ser Asp  Ala Leu Ala Lys Leu  Arg Lys Thr
1490                 1495                 1500

Ile Ile  Asn Glu Ser Leu Asn  Phe Lys Ile Arg Asp  Gln Leu Val
1505                 1510                 1515

Val Gly  Gln Leu Ile Pro Asp  Cys Tyr Val Glu Leu  Glu Lys Ile
1520                 1525                 1530

Ile Leu  Ser Glu Arg Lys Asn  Val Pro Ile Glu Phe  Pro Val Ile
1535                 1540                 1545

Asp Arg  Lys Arg Leu Leu Gln  Leu Val Arg Glu Asn  Gln Leu Gln
1550                 1555                 1560

Leu Asp  Glu Asn Glu Leu Pro  His Ala Val His Phe  Leu Asn Glu
1565                 1570                 1575

Ser Gly  Val Leu Leu His Phe  Gln Asp Pro Ala Leu  Gln Leu Ser
1580                 1585                 1590

Asp Leu  Tyr Phe Val Glu Pro  Lys Trp Leu Cys Lys  Ile Met Ala
1595                 1600                 1605

Gln Ile  Leu Thr Val Lys Val  Glu Gly Cys Pro Lys  His Pro Lys
1610                 1615                 1620

Gly Ile  Ile Ser Arg Arg Asp  Val Glu Lys Phe Leu  Ser Lys Lys
1625                 1630                 1635

Arg Lys  Phe Pro Lys Asn Tyr  Met Ser Gln Tyr Phe  Lys Leu Leu
1640                 1645                 1650

Glu Lys  Phe Gln Ile Ala Leu  Pro Ile Gly Glu Glu  Tyr Leu Leu
1655                 1660                 1665

Val Pro  Ser Ser Leu Ser Asp  His Arg Pro Val Ile  Glu Leu Pro
1670                 1675                 1680

His Cys  Glu Asn Ser Glu Ile  Ile Ile Arg Leu Tyr  Glu Met Pro
1685                 1690                 1695

Tyr Phe  Pro Met Gly Phe Trp  Ser Arg Leu Ile Asn  Arg Leu Leu
1700                 1705                 1710

Glu Ile  Ser Pro Tyr Met Leu  Ser Gly Arg Glu Arg  Ala Leu Arg
1715                 1720                 1725

Pro Asn  Arg Met Tyr Trp Arg  Gln Gly Ile Tyr Leu  Asn Trp Ser
1730                 1735                 1740

Pro Glu  Ala Tyr Cys Leu Val  Gly Ser Glu Val Leu  Asp Asn His
1745                 1750                 1755

Pro Glu  Ser Phe Leu Lys Ile  Thr Val Pro Ser Cys  Arg Lys Gly
1760                 1765                 1770

Cys Ile  Leu Leu Gly Gln Val  Val Asp His Ile Asp  Ser Leu Met
1775                 1780                 1785

Glu Glu  Trp Phe Pro Gly Leu  Leu Glu Ile Asp Ile  Cys Gly Glu
1790                 1795                 1800

Gly Glu  Thr Leu Leu Lys Lys  Trp Ala Leu Tyr Ser  Phe Asn Asp
1805                 1810                 1815

Gly Glu  Glu His Gln Lys Ile  Leu Leu Asp Asp Leu  Met Lys Lys
1820                 1825                 1830

Ala Glu  Glu Gly Asp Leu Leu  Val Asn Pro Asp Gln  Pro Arg Leu
1835                 1840                 1845

Thr Ile  Pro Ile Ser Gln Ile  Ala Pro Asp Leu Ile  Leu Ala Asp
1850                 1855                 1860

Leu Pro  Arg Asn Ile Met Leu  Asn Asn Asp Glu Leu  Glu Phe Glu
1865                 1870                 1875
```

-continued

```
Gln Ala  Pro Glu Phe Leu Leu  Gly Asp Gly Ser Phe  Gly Ser Val
1880                 1885                 1890

Tyr Arg  Ala Ala Tyr Glu Gly  Glu Glu Val Ala Val  Lys Ile Phe
1895                 1900                 1905

Asn Lys  His Thr Ser Leu Arg  Leu Leu Arg Gln Glu  Leu Val Val
1910                 1915                 1920

Leu Cys  His Leu His His Pro  Ser Leu Ile Ser Leu  Leu Ala Ala
1925                 1930                 1935

Gly Ile  Arg Pro Arg Met Leu  Val Met Glu Leu Ala  Ser Lys Gly
1940                 1945                 1950

Ser Leu  Asp Arg Leu Leu Gln  Gln Asp Lys Ala Ser  Leu Thr Arg
1955                 1960                 1965

Thr Leu  Gln His Arg Ile Ala  Leu His Val Ala Asp  Gly Leu Arg
1970                 1975                 1980

Tyr Leu  His Ser Ala Met Ile  Ile Tyr Arg Asp Leu  Lys Pro His
1985                 1990                 1995

Asn Val  Leu Leu Phe Thr Leu  Tyr Pro Asn Ala Ala  Ile Ile Ala
2000                 2005                 2010

Lys Ile  Ala Asp Tyr Xaa Ile  Ala Gln Tyr Cys Cys  Arg Met Gly
2015                 2020                 2025

Ile Lys  Thr Ser Glu Gly Thr  Pro Gly Phe Arg Ala  Pro Glu Val
2030                 2035                 2040

Ala Arg  Gly Asn Val Ile Tyr  Asn Gln Gln Ala Asp  Val Tyr Ser
2045                 2050                 2055

Phe Gly  Leu Leu Leu Tyr Asp  Ile Leu Thr Thr Gly  Gly Arg Ile
2060                 2065                 2070

Val Glu  Gly Leu Lys Phe Pro  Asn Glu Phe Asp Glu  Leu Glu Ile
2075                 2080                 2085

Gln Gly  Lys Leu Pro Asp Pro  Val Lys Glu Tyr Gly  Cys Ala Pro
2090                 2095                 2100

Trp Pro  Met Val Glu Lys Leu  Ile Lys Gln Cys Leu  Lys Glu Asn
2105                 2110                 2115

Pro Gln  Glu Arg Pro Thr Ser  Ala Gln Val Phe Asp  Ile Leu Asn
2120                 2125                 2130

Ser Ala  Glu Leu Val Cys Leu  Thr Arg Arg Ile Leu  Leu Pro Lys
2135                 2140                 2145

Asn Val  Ile Val Glu Cys Met  Val Ala Thr His His  Asn Ser Arg
2150                 2155                 2160

Asn Ala  Ser Ile Trp Leu Gly  Cys Gly His Thr Asp  Arg Gly Gln
2165                 2170                 2175

Leu Ser  Phe Leu Asp Leu Asn  Thr Glu Gly Tyr Thr  Ser Glu Glu
2180                 2185                 2190

Val Ala  Asp Ser Arg Ile Leu  Cys Leu Ala Leu Val  His Leu Pro
2195                 2200                 2205

Val Glu  Lys Glu Ser Trp Ile  Val Ser Gly Thr Gln  Ser Gly Thr
2210                 2215                 2220

Leu Leu  Val Ile Asn Thr Glu  Asp Gly Lys Lys Arg  His Thr Leu
2225                 2230                 2235

Glu Lys  Met Thr Asp Ser Val  Thr Cys Leu Tyr Cys  Asn Ser Phe
2240                 2245                 2250

Ser Lys  Gln Ser Lys Gln Lys  Asn Phe Leu Leu Val  Gly Thr Ala
2255                 2260                 2265

Asp Gly  Lys Leu Ala Ile Phe  Glu Asp Lys Thr Val  Lys Leu Lys
```

```
2270                2275                2280

Gly Ala  Ala Pro Leu Lys Ile  Leu Asn Ile Gly Asn  Val Ser Thr
2285                2290                2295

Pro Leu  Met Cys Leu Ser Glu  Ser Thr Asn Ser Thr  Glu Arg Asn
2300                2305                2310

Val Met  Trp Gly Gly Cys Gly  Thr Lys Ile Phe Ser  Phe Ser Asn
2315                2320                2325

Asp Phe  Thr Ile Gln Lys Leu  Ile Glu Thr Arg Thr  Ser Gln Leu
2330                2335                2340

Phe Ser  Tyr Ala Ala Phe Ser  Asp Ser Asn Ile Ile  Thr Val Val
2345                2350                2355

Val Asp  Thr Ala Leu Tyr Ile  Ala Lys Gln Asn Ser  Pro Val Val
2360                2365                2370

Glu Val  Trp Asp Lys Lys Thr  Glu Lys Leu Cys Gly  Leu Ile Asp
2375                2380                2385

Cys Val  His Phe Leu Arg Glu  Val Met Val Lys Glu  Asn Lys Glu
2390                2395                2400

Ser Lys  His Lys Met Ser Tyr  Ser Gly Arg Val Lys  Thr Leu Cys
2405                2410                2415

Leu Gln  Lys Asn Thr Ala Leu  Trp Ile Gly Thr Gly  Gly Gly His
2420                2425                2430

Ile Leu  Leu Leu Asp Leu Ser  Thr Arg Arg Leu Ile  Arg Val Ile
2435                2440                2445

Tyr Asn  Phe Cys Asn Ser Val  Arg Val Met Met Thr  Ala Gln Leu
2450                2455                2460

Gly Ser  Leu Lys Asn Val Met  Leu Val Leu Gly Tyr  Asn Arg Lys
2465                2470                2475

Asn Thr  Glu Gly Thr Gln Lys  Gln Lys Glu Ile Gln  Ser Cys Leu
2480                2485                2490

Thr Val  Trp Asp Ile Asn Leu  Pro His Glu Val Gln  Asn Leu Glu
2495                2500                2505

Lys His  Ile Glu Val Arg Lys  Glu Leu Ala Glu Lys  Met Arg Arg
2510                2515                2520

Thr Ser  Val Glu
2525
```

<210> SEQ ID NO 2
<211> LENGTH: 7584
<212> TYPE: DNA
<213> ORGANISM: Homo sapiens
<220> FEATURE:
<221> NAME/KEY: misc_feature
<222> LOCATION: (6055)..(6055)
<223> OTHER INFORMATION: n may be a, c or t.
<220> FEATURE:
<221> NAME/KEY: misc_feature
<222> LOCATION: (5457)..(5457)
<223> OTHER INFORMATION: n may be c or t.
<220> FEATURE:
<221> NAME/KEY: misc_feature
<222> LOCATION: (5096)..(5096)
<223> OTHER INFORMATION: n may be a or g.
<220> FEATURE:
<221> NAME/KEY: misc_feature
<222> LOCATION: (4321)..(4321)
<223> OTHER INFORMATION: n may be c or t.
<220> FEATURE:
<221> NAME/KEY: misc_feature
<222> LOCATION: (3364)..(3364)
<223> OTHER INFORMATION: n may be a or g.
<220> FEATURE:

<221> NAME/KEY: misc_feature
<222> LOCATION: (149)..(149)
<223> OTHER INFORMATION: n may be a or g.
<300> PUBLICATION INFORMATION:
<308> DATABASE ACCESSION NUMBER: Genbank / AY792511
<309> DATABASE ENTRY DATE: 2004-11-15
<313> RELEVANT RESIDUES: (1)..(7584)

<400> SEQUENCE: 2

```
atggctagtg gcagctgtca ggggtgcgaa gaggacgagg aaactctgaa gaagttgata     60

gtcaggctga acaatgtcca ggaaggaaaa cagatagaaa cgctggtcca aatcctggag    120

gatctgctgg tgttcacgta ctccgagcnc gcctccaagt tatttcaagg caaaaatatc    180

catgtgcctc tgttgatcgt cttggactcc tatatgagag tcgcgagtgt gcagcaggtg    240

ggttggtcac ttctgtgcaa attaatagaa gtctgtccag gtacaatgca aagcttaatg    300

ggaccccagg atgttggaaa tgattgggaa gtccttggtg ttcaccaatt gattcttaaa    360

atgctaacag ttcataatgc cagtgtaaac ttgtcagtga ttggactgaa gaccttagat    420

ctcctcctaa cttcaggtaa aatcaccttg ctgatactgg atgaagaaag tgatattttc    480

atgttaattt ttgatgccat gcactcattt ccagccaatg atgaagtcca gaaacttgga    540

tgcaaagctt tacatgtgct gtttgagaga gtctcagagg agcaactgac tgaatttgtt    600

gagaacaaag attatatgat attgttaagt gcgtcaacaa attttaaaga tgaagaggaa    660

attgtgcttc atgtgctgca ttgtttacat tccctagcga ttccttgcaa taatgtggaa    720

gtcctcatga gtggcaatgt caggtgttat aatattgtgg tggaagctat gaaagcattc    780

cctatgagtg aaagaattca agaagtgagt tgctgtttgc tccataggct tacattaggt    840

aatttttttca atatcctggt attaaacgaa gtccatgagt ttgtggtgaa agctgtgcag    900

cagtacccag agaatgcagc attgcagatc tcagcgctca gctgtttggc cctcctcact    960

gagactattt tcttaaatca agatttagag gaaaagaatg agaatcaaga gaatgatgat   1020

gagggggaag aagataaatt gttttggctg gaagcctgtt acaaagcatt aacgtggcat   1080

agaaagaaca agcacgtgca ggaggccgca tgctgggcac taaataatct ccttatgtac   1140

caaaacagtt tacatgagaa gattggagat gaagatggcc atttcccagc tcatagggaa   1200

gtgatgctct ccatgctgat gcattcttca tcaaaggaag ttttccaggc atctgcgaat   1260

gcattgtcaa ctctcttaga acaaaatgtt aatttcagaa aaatactgtt atcaaaagga   1320

atacacctga atgttttgga gttaatgcag aagcatatac attctcctga agtggctgaa   1380

agtggctgta aaatgctaaa tcatcttttt gaaggaagca acacttccct ggatataatg   1440

gcagcagtgg tccccaaaat actaacagtt atgaaacgtc atgagacatc attaccagtg   1500

cagctggagg cgcttcgagc tattttacat tttatagtgc ctggcatgcc agaagaatcc   1560

agggaggata cagaatttca tcataagcta aatatggtta aaaaacagtg tttcaagaat   1620

gatattcaca aactggtcct agcagctttg aacaggttca ttggaaatcc tgggattcag   1680

aaatgtggat taaaagtaat ttcttctatt gtacattttc ctgatgcatt agagatgtta   1740

tccctggaag gtgctatgga ttcagtgctt cacacactgc agatgtatcc agatgaccaa   1800

gaaattcagt gtctgggttt aagtcttata ggatacttga ttacaaagaa gaatgtgttc   1860

ataggaactg gacatctgct ggcaaaaatt ctggtttcca gcttataccg atttaaggat   1920

gttgctgaaa tacagactaa aggatttcag acaatcttag caatcctcaa attgtcagca   1980

tctttttcta agctgctggt gcatcattca tttgacttag taatattcca tcaaatgtct   2040

tccaatatca tggaacaaaa ggatcaacag tttctaaacc tctgttgcaa gtgttttgca   2100
```

-continued

```
aaagtagcta tggatgatta cttaaaaaat gtgatgctag agagagcgtg tgatcagaat   2160
aacagcatca tggttgaatg cttgcttcta ttgggagcag atgccaatca agcaaaggag   2220
ggatcttctt taatttgtca ggtatgtgag aaagagagca gtcccaaatt ggtggaactc   2280
ttactgaata gtggatctcg tgaacaagat gtacgaaaag cgttgacgat aagcattggg   2340
aaaggtgaca gccagatcat cagcttgctc ttaaggaggc tggccctgga tgtggccaac   2400
aatagcattt gccttggagg attttgtata ggaaaagttg aaccttcttg gcttggtcct   2460
ttatttccag ataagacttc taatttaagg aaacaaacaa atatagcatc tacactagca   2520
agaatggtga tcagatatca gatgaaaagt gctgtggaag aaggaacagc ctcaggcagc   2580
gatggaaatt tttctgaaga tgtgctgtct aaatttgatg aatggacctt tattcctgac   2640
tcttctatgg acagtgtgtt tgctcaaagt gatgacctgg atagtgaagg aagtgaaggc   2700
tcatttcttg tgaaaaagaa atctaattca attagtgtag gagaatttta ccgagatgcc   2760
gtattacagc gttgctcacc aaatttgcaa agacattcca attccttggg gcccattttt   2820
gatcatgaag atttactgaa gcgaaaaaga aaaatactat cttcagatga ttcactcagg   2880
tcatcaaaac ttcaatccca tatgaggcat tcagacagca tttcttctct ggcttctgag   2940
agagaatata ttacatcact agacctttca gcaaatgaac taagagatat tgatgcccta   3000
agccagaaat gctgtataag tgttcatttg gagcatcttg aaaagctgga gcttcaccag   3060
aatgcactca cgagctttcc acaacagcta tgtgaaactc tgaagagttt gacacatttg   3120
gacttgcaca gtaataaatt tacatcattt ccttcttatt tgttgaaaat gagttgtatt   3180
gctaatcttg atgtctctcg aaatgacatt ggaccctcag tggttttaga tcctacagtg   3240
aaatgtccaa ctctgaaaca gtttaacctg tcatataacc agctgtcttt tgtacctgag   3300
aacctcactg atgtggtaga gaaactggag cagctcattt tagaaggaaa taaaatatca   3360
gggntatgct ccccccttgag actgaaggaa ctgaagattt taaaccttag taagaaccac   3420
atttcatccc tatcagagaa ctttcttgag gcttgtccta aagtggagag tttcagtgcc   3480
agaatgaatt ttcttgctgc tatgcctttc ttgcctcctt ctatgacaat cctaaaatta   3540
tctcagaaca aattttcctg tattccagaa gcaattttaa atcttccaca cttgcggtct   3600
ttagatatga gcagcaatga tattcagtac ctaccaggtc ccgcacactg gaaatctttg   3660
aacttaaggg aactcttatt tagccataat cagatcagca tcttggactt gagtgaaaaa   3720
gcatatttat ggtctagagt agagaaactg catctttctc acaataaact gaaagagatt   3780
cctcctgaga ttggctgtct tgaaaatctg acatctctgg atgtcagtta caacttggaa   3840
ctaagatcct ttcccaatga aatggggaaa ttaagcaaaa tatgggatct tcctttggat   3900
gaactgcatc ttaactttga ttttaaacat ataggatgta aagccaaaga catcataagg   3960
tttcttcaac agcgattaaa aaaggctgtg ccttataacc gaatgaaact tatgattgtg   4020
ggaaatactg ggagtggtaa aaccacctta ttgcagcaat taatgaaaac caagaaatca   4080
gatcttggaa tgcaaagtgc cacagttggc atagatgtga aagactggcc tatccaaata   4140
agagacaaaa gaaagagaga tctcgtccta aatgtgtggg attttgcagg tcgtgaggaa   4200
ttctatagta ctcatcccca ttttatgacg cagcgagcat tgtaccttgc tgtctatgac   4260
ctcagcaagg gacaggctga agttgatgcc atgaagcctt ggctcttcaa tataaaggct   4320
ngcgcttctt cttcccctgt gattctcgtt ggcacacatt tggatgtttc tgatgagaag   4380
caacgcaaag cctgcatgag taaaatcacc aaggaactcc tgaataagcg agggttccct   4440
```

-continued

```
gccatacgag attaccactt tgtgaatgcc accgaggaat ctgatgcttt ggcaaaactt   4500
cggaaaacca tcataaacga gagccttaat ttcaagatcc gagatcagct tgttgttgga   4560
cagctgattc cagactgcta tgtagaactt gaaaaaatca ttttatcgga gcgtaaaaat   4620
gtgccaattg aatttcccgt aattgaccgg aaacgattat tacaactagt gagagaaaat   4680
cagctgcagt tagatgaaaa tgagcttcct cacgcagttc actttctaaa tgaatcagga   4740
gtccttcttc attttcaaga cccagcactg cagttaagtg acttgtactt tgtggaaccc   4800
aagtggcttt gtaaaatcat ggcacagatt ttgacagtga aagtggaagg ttgtccaaaa   4860
caccctaagg gcattatttc gcgtagagat gtggaaaaat ttctttcaaa aaaaaggaaa   4920
tttccaaaga actacatgtc acagtatttt aagctcctag aaaaattcca gattgctttg   4980
ccaataggag aagaatattt gctggttcca agcagtttgt ctgaccacag gcctgtgata   5040
gagcttcccc attgtgagaa ctctgaaatt atcatccgac tatatgaaat gccttntttt   5100
ccaatgggat tttggtcaag attaatcaat cgattacttg agatttcacc ttacatgctt   5160
tcagggagag aacgagcact tcgcccaaac agaatgtatt ggcgacaagg catttactta   5220
aattggtctc ctgaagctta ttgtctggta ggatctgaag tcttagacaa tcatccagag   5280
agtttcttaa aaattacagt tccttcttgt agaaaaggct gtattctttt gggccaagtt   5340
gtggaccaca ttgattctct catggaagaa tggtttcctg ggttgctgga gattgatatt   5400
tgtggtgaag gagaaactct gttgaagaaa tgggcattat atagttttaa tgatggngaa   5460
gaacatcaaa aaatcttact tgatgacttg atgaagaaag cagaggaagg agatctctta   5520
gtaaatccag atcaaccaag gctcaccatt ccaatatctc agattgcccc tgacttgatt   5580
ttggctgacc tgcctagaaa tattatgttg aataatgatg agttggaatt tgaacaagct   5640
ccagagtttc tcctaggtga tggcagtttt ggatcagttt accgagcagc ctatgaagga   5700
gaagaagtgg ctgtgaagat ttttaataaa catacatcac tcaggctgtt aagacaagag   5760
cttgtggtgc tttgccacct ccaccacccc agtttgatat ctttgctggc agctgggatt   5820
cgtccccgga tgttggtgat ggagttagcc tccaagggtt ccttggatcg cctgcttcag   5880
caggacaaag ccagcctcac tagaacccta cagcacagga ttgcactcca cgtagctgat   5940
ggtttgagat acctccactc agccatgatt atataccgag acctgaaacc ccacaatgtg   6000
ctgcttttca cactgtatcc caatgctgcc atcattgcaa agattgctga ctacngcatt   6060
gctcagtact gctgtagaat ggggataaaa acatcagagg gcacaccagg gtttcgtgca   6120
cctgaagttg ccagaggaaa tgtcatttat aaccaacagg ctgatgttta ttcatttggt   6180
ttactactct atgacatttt gacaactgga ggtagaatag tagagggttt gaagtttcca   6240
aatgagtttg atgaattaga aatacaagga aaattacctg atccagttaa agaatatggt   6300
tgtgccccat ggcctatggt tgagaaatta attaaacagt gtttgaaaga aaatcctcaa   6360
gaaaggccta cttctgccca ggtctttgac attttgaatt cagctgaatt agtctgtctg   6420
acgagacgca ttttattacc taaaaacgta attgttgaat gcatggttgc tacacatcac   6480
aacagcagga atgcaagcat ttggctgggc tgtgggcaca ccgacagagg acagctctca   6540
tttcttgact taaatactga aggatacact tctgaggaag ttgctgatag tagaatattg   6600
tgcttagcct tggtgcatct tcctgttgaa aaggaaagct ggattgtgtc tgggacacag   6660
tctggtactc tcctggtcat caataccgaa gatgggaaaa agagacatac cctagaaaag   6720
atgactgatt ctgtcacttg tttgtattgc aattcctttt ccaagcaaag caaacaaaaa   6780
aattttcttt tggttggaac cgctgatggc aagttagcaa tttttgaaga taagactgtt   6840
```

-continued

```
aagcttaaag gagctgctcc tttgaagata ctaaatatag gaaatgtcag tactccattg   6900
atgtgtttga gtgaatccac aaattcaacg gaaagaaatg taatgtgggg aggatgtggc   6960
acaaagattt tctccttttc taatgatttc accattcaga aactcattga gacaagaaca   7020
agccaactgt tttcttatgc agctttcagt gattccaaca tcataacagt ggtggtagac   7080
actgctctct atattgctaa gcaaaatagc cctgttgtgg aagtgtggga taagaaaact   7140
gaaaaactct gtggactaat agactgcgtg cactttttaa gggaggtaat ggtaaaagaa   7200
aacaaggaat caaaacacaa aatgtcttat tctgggagag tgaaaaccct ctgccttcag   7260
aagaacactg ctctttggat aggaactgga ggaggccata ttttactcct ggatctttca   7320
actcgtcgac ttatacgtgt aatttacaac ttttgtaatt cggtcagagt catgatgaca   7380
gcacagctag gaagccttaa aaatgtcatg ctggtattgg gctacaaccg gaaaaatact   7440
gaaggtacac aaaagcagaa agagatacaa tcttgcttga ccgtttggga catcaatctt   7500
ccacatgaag tgcaaaattt agaaaaacac attgaagtga gaaaagaatt agctgaaaaa   7560
atgagacgaa catctgttga gtaa                                          7584

12
```